(12) United States Patent
Setlak et al.

(10) Patent No.: US 9,322,794 B2
(45) Date of Patent: Apr. 26, 2016

(54) BIOMETRIC FINGER SENSOR INCLUDING ARRAY SHIELDING ELECTRODE AND RELATED METHODS

(71) Applicant: Apple Inc., Cupertino, CA (US)

(72) Inventors: Dale R. Setlak, Melbourne, FL (US); Giovanni Gozzini, Berkeley, CA (US)

(73) Assignee: APPLE INC., Cupertino, CA (US)

( * ) Notice: Subject to any disclaimer, the term of this patent is extended or adjusted under 35 U.S.C. 154(b) by 537 days.

(21) Appl. No.: 13/718,307

(22) Filed: Dec. 18, 2012

(65) Prior Publication Data

US 2014/0171158 A1  Jun. 19, 2014

(51) Int. Cl.
*G01N 27/02* (2006.01)
*G06K 9/00* (2006.01)
*G06F 21/32* (2013.01)

(52) U.S. Cl.
CPC .............. *G01N 27/02* (2013.01); *G06F 21/32* (2013.01); *G06K 9/00* (2013.01); *G06K 9/0002* (2013.01); *G06K 9/00053* (2013.01); *Y10T 29/49204* (2015.01)

(58) Field of Classification Search
CPC ... G06K 9/0002; G06K 9/00053; G06K 9/00; G06F 2203/0338; G06F 3/03547; G06F 21/32; G06F 3/044; G01N 27/02
See application file for complete search history.

(56) References Cited

U.S. PATENT DOCUMENTS

| | | | |
|---|---|---|---|
| 5,430,381 A * | 7/1995 | Dower ................. | G01B 7/34 324/452 |
| 5,940,526 A | 8/1999 | Setlak et al. | |
| 5,953,441 A | 9/1999 | Setlak | |
| 5,963,679 A * | 10/1999 | Setlak ................. | 382/312 |
| 6,088,471 A | 7/2000 | Setlak et al. | |
| 6,097,195 A | 8/2000 | Ackland et al. | |
| 6,289,114 B1 | 9/2001 | Mainguet | |
| 6,370,965 B1 * | 4/2002 | Knapp ................. | 73/862.046 |
| 6,429,666 B1 * | 8/2002 | Um ................ | G01R 27/2605 324/693 |
| 6,628,812 B1 | 9/2003 | Setlak et al. | |
| 6,927,581 B2 | 8/2005 | Gozzini | |
| 7,361,919 B2 | 4/2008 | Setlak | |
| 7,697,281 B2 | 4/2010 | Dabov et al. | |
| 7,697,729 B2 | 4/2010 | Howell et al. | |
| 7,715,593 B1 | 5/2010 | Adams et al. | |
| 7,734,068 B2 | 6/2010 | Fisher | |
| 7,809,168 B2 | 10/2010 | Abiko et al. | |
| 8,145,916 B2 | 3/2012 | Boshra et al. | |
| 2001/0025532 A1 * | 10/2001 | Kramer ................ | A61B 5/1172 73/862.68 |
| 2003/0016024 A1 * | 1/2003 | Teranuma et al. ........... | 324/519 |
| 2003/0165261 A1 * | 9/2003 | Johansen et al. ............. | 382/124 |
| 2003/0173982 A1 * | 9/2003 | Ishii et al. .................... | 324/663 |

(Continued)

FOREIGN PATENT DOCUMENTS

| | | |
|---|---|---|
| EP | 0791899 | 8/1997 |
| EP | 1406069 | 4/2004 |
| WO | 2005124659 | 12/2005 |

*Primary Examiner* — Claire X Pappas
*Assistant Examiner* — Benjamin Casarez
(74) *Attorney, Agent, or Firm* — Allen, Dyer, Doppelt, Milbrath & Gilchrist, P.A.

(57) ABSTRACT

A biometric finger sensor may include an array of biometric finger sensing pixels and an array shielding electrode outside the array of biometric finger sensing pixels. The biometric finger sensor may further include a finger drive electrode outside the array shielding electrode. Finger drive circuitry may generate a finger drive signal for the finger drive electrode and generate a compensating finger drive signal for the shielding electrode.

27 Claims, 8 Drawing Sheets

(56) References Cited

U.S. PATENT DOCUMENTS

| | | | |
|---|---|---|---|
| 2004/0096061 A1* | 5/2004 | Yano et al. .................. 380/59 |
| 2004/0230810 A1 | 11/2004 | Hillhouse |
| 2005/0069178 A1* | 3/2005 | Nysaether et al. ............ 382/124 |
| 2005/0110103 A1* | 5/2005 | Setlak .......................... 257/414 |
| 2005/0253598 A1 | 11/2005 | Kawahata |
| 2006/0034499 A1* | 2/2006 | Shinoda et al. .............. 382/124 |
| 2006/0049834 A1* | 3/2006 | Umeda ......................... 324/658 |
| 2006/0203403 A1* | 9/2006 | Schediwy et al. .............. 361/56 |
| 2007/0139049 A1* | 6/2007 | Van Berkel ......... G06K 9/0002 324/452 |
| 2008/0069413 A1* | 3/2008 | Riedijk et al. ................ 382/124 |
| 2008/0079442 A1* | 4/2008 | Posamentier ................ 324/605 |
| 2008/0219522 A1 | 9/2008 | Hook |
| 2009/0083850 A1* | 3/2009 | Fadell et al. .................... 726/19 |
| 2009/0316963 A1 | 12/2009 | Boshra |
| 2010/0082444 A1 | 4/2010 | Lin et al. |
| 2010/0321158 A1 | 12/2010 | Setlak et al. |
| 2011/0090047 A1* | 4/2011 | Patel ........................... 340/5.82 |
| 2011/0175703 A1 | 7/2011 | Benkley, III |
| 2012/0242635 A1 | 9/2012 | Erhart et al. |
| 2012/0280698 A1* | 11/2012 | Oya ............................. 324/658 |
| 2013/0341398 A1* | 12/2013 | Rao .............................. 235/439 |

* cited by examiner

BIOMETRIC FINGER SENSOR INCLUDING ARRAY SHIELDING ELECTRODE AND RELATED METHODS

FIELD OF THE INVENTION

The present invention relates to the field of electronics, and, more particularly, to finger sensing devices and related methods.

BACKGROUND OF THE INVENTION

Fingerprint sensing and matching is a reliable and widely used technique for personal identification or verification. In particular, a common approach to fingerprint identification involves scanning a sample fingerprint or an image thereof and storing the image and/or unique characteristics of the fingerprint image. The characteristics of a sample fingerprint may be compared to information for reference fingerprints already in a database to determine proper identification of a person, such as for verification purposes.

A particularly advantageous approach to fingerprint sensing is disclosed in U.S. Pat. No. 5,953,441 to Setlak and assigned to the assignee of the present invention, the entire contents of which are herein incorporated by reference. The fingerprint sensor is an integrated circuit sensor that drives the user's finger with an electric field signal and senses the electric field with an array of electric field sensing pixels on the integrated circuit substrate.

U.S. Pat. No. 6,289,114 to Mainguet, which is assigned to the assignee of the present invention and is incorporated in its entirety by reference, discloses a fingerprint sensor that includes a finger sensing integrated circuit (IC). The finger sensing IC includes a layer of piezoelectric or pyroelectric material placed between upper and lower electrodes to provide electric signals representative of an image of the ridges and valleys of the fingerprint.

A particularly advantageous approach to multi-biometric fingerprint sensing is disclosed in U.S. Pat. No. 7,361,919 to Setlak, which is assigned to the assignee of the present invention and is incorporated in its entirety by reference. The Setlak patent discloses a multi-biometric finger sensor sensing different biometric characteristics of a user's finger that have different matching selectivities.

A fingerprint sensor may be particularly advantageous for verification and/or authentication in an electronic device, and more particularly, a portable device, for example. Such a fingerprint sensor may be carried by the housing of a portable electronic device, for example, and may be sized to sense a fingerprint from a single-finger. For example, the AES3400 sensor from AuthenTec, Inc. of Melbourne, Fla., the assignee of the present invention, is widely used in a variety of notebooks, desktops and PC peripherals. Other fingerprint sensors, for example, the AES850, also from AuthenTec, Inc. of Melbourne, Fla., is a multi-function smart sensor that expands touch-based functionality of touchscreen and QWERTY smartphones with a reduced impact on sensor performance or durability. Thus, a fingerprint sensor may be particularly advantageous for providing more convenient access to the electronic device without a password, for example, and, more particularly, without having to type the password, which is often time consuming. A fingerprint sensor may also be particularly advantageous for starting one or more applications on the electronic device.

U.S. Patent Application Publication No. 2011/0175703 to Benkley, III discloses an electronic imager using an impedance sensor grid array mounted on or about a switch. More particularly, Benkley, III discloses a switch being incorporated into a sensor assembly that allows integration of sensor operations, such as, fingerprint sensor operations. A fingerprint sensor can be used for authentication while being used together with a power switch or navigation selection switch. The authentication may be used to access the device entirely or access different levels of information.

U.S. Patent Application Publication No. 2009/0083850 to Fadell et al. discloses an embedded authentication system in an electronic device. More particularly, Fadell et al. discloses authenticating a user via a fingerprint to provide access to resources or content that was previously not available. The electronic device may allow a user to authenticate for a particular amount of time for accessing restricted resources.

U.S. Pat. No. 7,809,168 to Abiko et al. discloses a biometric information input device. More particularly, Abiko et al. discloses a movement direction detection means for detecting a movement direction of a finger with respect to the fingerprint sensor, based on partial fingerprint images collected by the fingerprint sensor.

Moreover, while a fingerprint sensor used in an electronic device may be particularly advantageous for authentication, navigation, etc., these finger sensors generally require the user's finger to be placed in a very close proximity to the array of finger sensing pixels. The need for close proximity to the user's finger typically makes the mechanical packaging and the integration of a fingerprint sensor into the electronic device more difficult and more costly.

Some approaches to address packaging of an electronic device include a special molded package with an opening in the molding allowing the finger a close approach to the finger sensing array. Specialized packaging increases the cost of these sensors.

The desire for the user's finger to be close to the array of finger sensing pixels may limit the thickness of the material that can be placed over the array of finger sensing pixels, which may increasingly restrict the use of both protective and cosmetic coatings over the array area. Mechanically integrating these sensors into their host devices typically requires that the finger sensor project through a hole in the electronic device's case, so that the array of finger sensing pixels can be located about flush with the external surface of the case.

However, a negative aspect of these mounting arrangements may include increased difficulty and cost to seal the opening for the finger sensor in the electronic device case or housing against the ingress of moisture, dust, and other contaminants. Additionally, the opening in the case or housing with the finger sensor protruding may be cosmetically unacceptable to the intended appearance of the electronic device, and mounting the finger sensor in an opening in the case may be difficult and costly in some devices.

It may be desirable to extend the range of electric field based finger sensors so that they can image fingers through significantly thicker dielectric materials such as molded plastic structures. Using an increased thickness material layer over the array of finger sensing pixels may result in increased power consumption. More particularly, an increased thickness material layer generally requires a greater drive voltage to be driven into the user's finger. The greater distance from the array of finger sensing pixels and the increased drive voltage may result in increased noise of a finger image, which may be undesirable for authentication, for example.

SUMMARY OF THE INVENTION

In view of the foregoing background, it is therefore an object of the present invention to provide a biometric finger sensor that can generate a reduced noise finger image from a finger positioned at a relatively large distance from the array of biometric finger sensing pixels.

This and other objects, features, and advantages in accordance with the present invention are provided by a biometric finger sensor that may include an array of biometric finger sensing pixels, and an array shielding electrode outside the array of biometric finger sensing pixels. The finger biometric sensor may further include a finger drive electrode outside the array shielding electrode. Finger drive circuitry may generate a finger drive signal for the finger drive electrode and generate a compensating finger drive signal for the array shielding electrode. Accordingly, the biometric finger sensor may generate a reduced noise finger image from a finger positioned at a relatively large distance from the array of finger sensing pixels.

The finger drive circuitry may generate an inverted finger drive signal for the array shielding electrode, for example. The array shielding electrode may include a plurality of shielding pixels.

The biometric finger sensor may further include a ground electrode between the array shielding electrode and the array of biometric finger sensing pixels, for example. The biometric finger sensor may also include a dummy biometric finger sensing pixel area between the array of biometric finger sensing pixels and the ground electrode.

The biometric finger sensor may further include a dielectric routing substrate having a first surface adjacent the array of biometric finger sensing pixels, and a second surface adjacent the array shielding electrode and the finger drive electrode, for example.

The biometric finger sensor may further include a dielectric cap over the array of biometric finger sensing pixels, the finger drive electrode, and the finger drive circuitry. The dielectric cap may have a curved upper surface, for example.

The biometric finger sensor may also include a semiconductor substrate carrying the array of biometric finger sensing pixels. The array of biometric finger sensing pixels may include an array of electric field finger sensing pixels, for example.

A method aspect is directed to a method of making a biometric finger sensor. The method may include forming an array shielding electrode outside an array of biometric finger sensing pixels, and forming a finger drive electrode outside the array shielding electrode. The method also includes coupling finger drive circuitry to generate a finger drive signal for the finger drive electrode and generate a compensating finger drive signal for the array shielding electrode, for example.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to refer to like elements in different embodiments.

Figure 1:
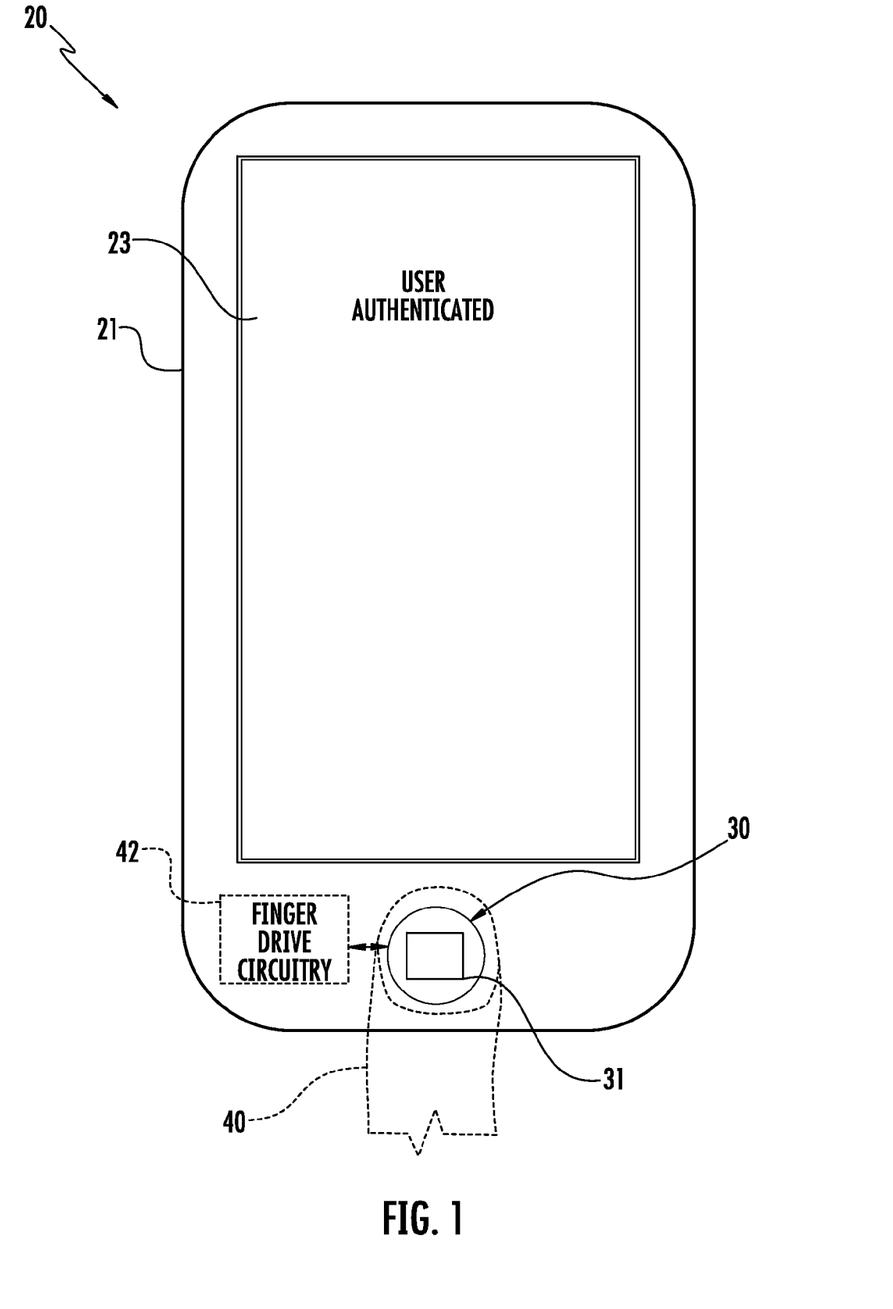
FIG. 1 is a plan view of an electronic device including a biometric finger sensor in accordance with the present invention.
Figure 2:
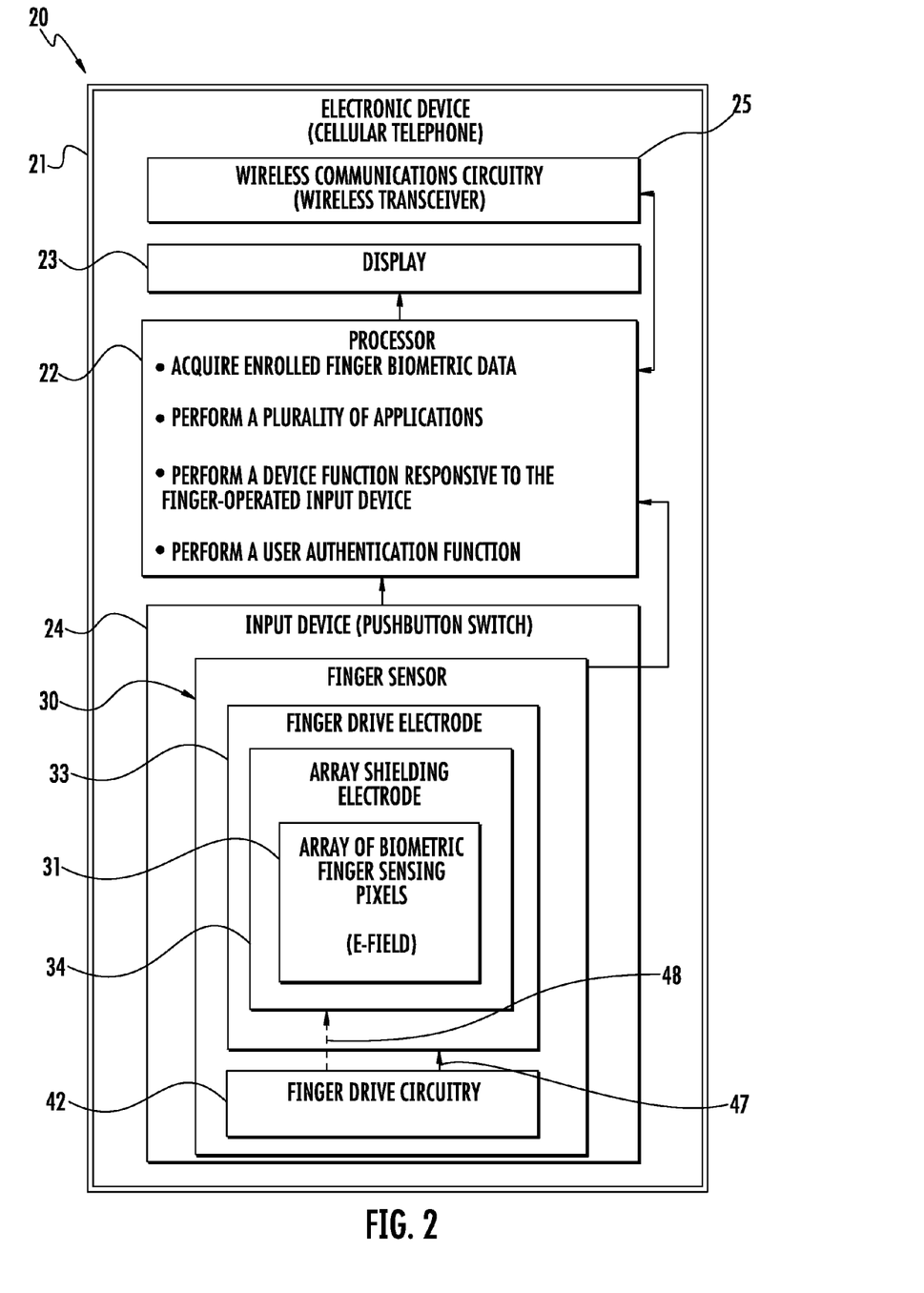
FIG. 2 is a schematic block diagram of the electronic device and biometric finger sensor of FIG. 1.

Referring initially to FIGS. 1 and 2, an electronic device 20 is now described. The electronic device 20 illustratively includes a portable housing 21 and a processor 22 carried by the portable housing. The electronic device 20 is illustratively a mobile wireless communications device, for example, a cellular telephone or smartphone. The electronic device 20 may be another type of electronic device, for example, a tablet computer, laptop computer, etc.

A wireless transceiver 25 is also carried within the portable housing 21 and is coupled to the processor 22. The wireless transceiver 25 cooperates with the processor 22 to perform at least one wireless communications function, for example, for voice and/or data communication. In some embodiments, the electronic device 20 may not include a wireless transceiver 25 or other wireless communications circuitry.

A display 23 is also carried by the portable housing 21 and is coupled to the processor 22. The display 23 may be a liquid crystal display (LCD), for example, or may be another type of display, as will be appreciated by those skilled in the art.

A finger-operated input device, illustratively in the form of a pushbutton switch 24, is also carried by the portable housing 21 and is coupled to the processor 22. The pushbutton switch 24 cooperates with the processor 22 to perform one or more device functions in response to operation of the pushbutton switch. For example, a device function may include a powering on or off of the electronic device 20, initiating communication via the wireless communications circuitry 25, and/or performing a menu function.

More particularly, with respect to a menu function, the processor 22 may change the display 23 to show a menu of available applications based upon pressing of the pushbutton switch 24. In other words, the pushbutton switch 24 may be a home switch or button, or key. The processor 22 may also toggle between applications executed by the processor based upon pressing of the pushbutton switch 24. Of course, other device functions may be performed based upon the pushbutton switch 24 for example, finger biometric data enrollment and/or finger biometric data matching. In some embodiments, the finger-operated input device 24 may be a different type of finger-operated input device, for example, forming part of a touch screen display. Other or additional finger-operated input devices may be carried by the portable housing 21.

Figure 3:
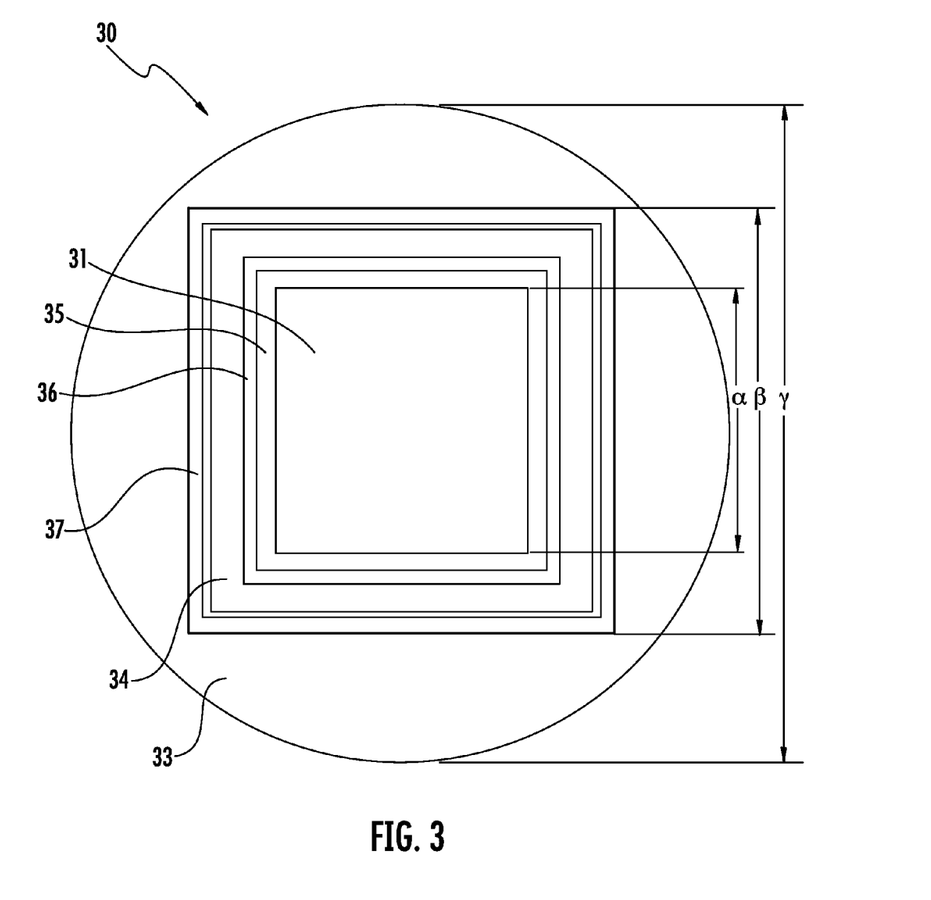
FIG. 3 is a top view of the biometric finger sensor of FIG. 1.
Figure 4:
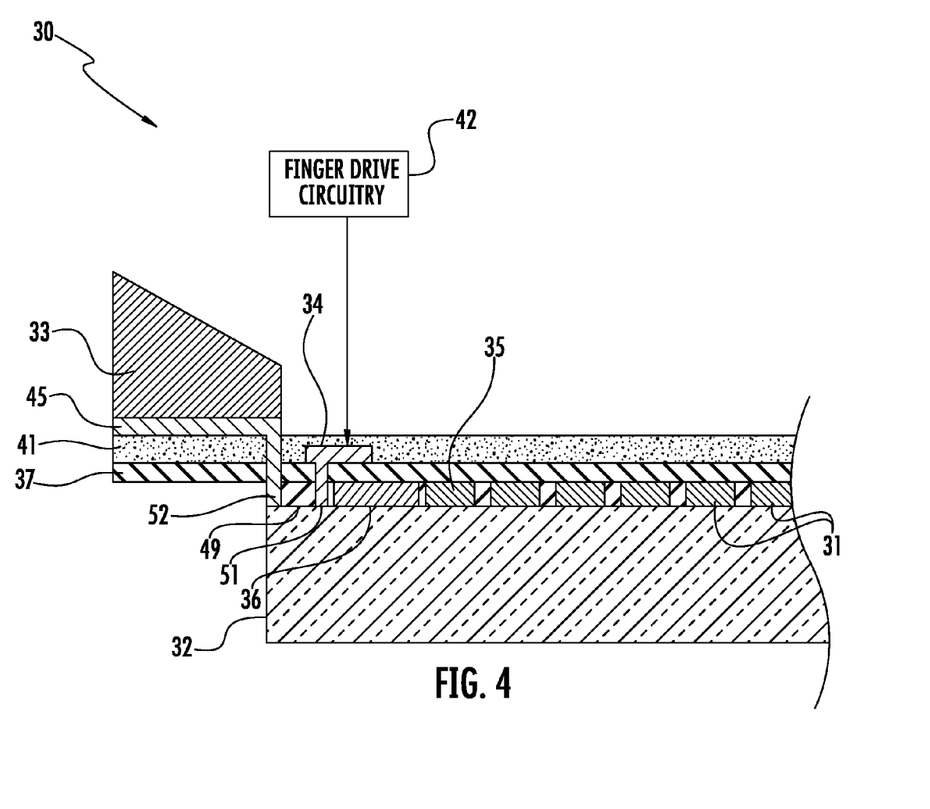
FIG. 4 is a cross-sectional view of a portion of the biometric finger sensor of FIG. 3.
Figure 5:
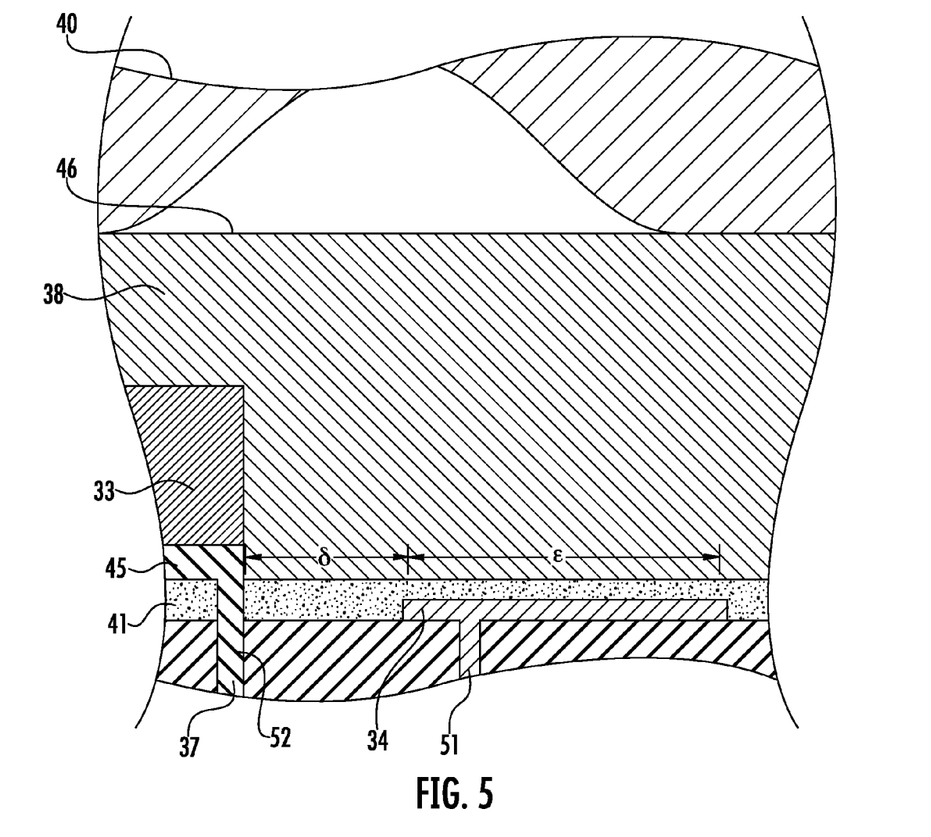
FIG. 5 is an enlarged cross-sectional view of a portion of the biometric finger sensor of FIG. 1.

Referring now additionally to FIGS. 3-5, a biometric finger sensor 30 is carried by the pushbutton switch 24 to sense a user's finger 40. The finger sensor 30 is carried by the pushbutton switch 24 so that when a user contacts and/or presses downward on the pushbutton switch, finger biometric data from the user's finger 40 is acquired, for example, for finger matching and/or finger enrollment to be stored and later used for matching.

The finger biometric data may include fingerprint minutae data, ridge and/or valley fingerprint image data, ridge flow data, finger pore data, etc. For example, the biometric finger sensor 30 may be a finger sensor as described in U.S. Pat. No. 5,953,441 to Setlak and/or as described in U.S. Pat. No. 6,927,581 to Gozzini, and assigned to the assignee of the present invention and the entire contents of which are herein incorporated by reference.

The biometric finger sensor 30 includes an array of biometric finger sensing pixels 31 to receive a user's finger 40 adjacent thereto. The array of finger biometric sensing pixels 31 are carried by a semiconductor substrate 32, for example, a silicon substrate. The array of finger sensing pixels 31 may be any array size, as will be appreciated by those skilled in the art, but may be particularly sized to be carried by the pushbutton switch 24. The array of biometric finger sensing pixels 31 are illustratively in the shape of a square. In some embodiments, the array of biometric finger sensing pixels 31 may have a different shape.

Each biometric finger sensing pixel 31 may be an electric-field sensing pixel, and more particularly, a high impedance electric field sensing pixel. In some embodiments, each finger sensing pixel may be a capacitive sensing pixel, for example, or other type of sensing pixel. As will be appreciated by those skilled in the art, each finger sensing pixel 31 includes a finger sensing electrode.

The biometric finger sensor 30 further includes a dummy biometric finger sensing pixel area 35 carried by the semiconductor substrate 32 and laterally outside the array of biometric finger sensing pixels 31. The dummy biometric finger sensing pixel area 35 includes dummy pixels which are unused for biometric finger sensing. The dummy pixels of the dummy biometric finger sensing pixel area 35 may be coupled a voltage reference, for example a ground, or may be electrically floating.

A ground electrode 36 is also carried by the semiconductor substrate 32 and laterally outside the array of biometric finger sensing pixels 31, or more particularly, outside the dummy biometric finger sensing pixel area 35. In other words, the dummy biometric finger sensing pixel area 35 is laterally between the ground electrode 36 and the array of biometric finger sensing pixels 31. The dummy biometric finger sensing pixel area 35 and the ground electrode 36 are illustratively in the shape of a square ring following the square shape of the array of biometric finger sensing pixels 31. In some embodiments, the dummy biometric finger sensing pixel area 35 and the ground electrode 36 may not be square and/or ring-shaped, for example, each of the dummy biometric finger sensing pixel area and the ground electrode may be a circular ring and/or may have one or more discontinuities therein.

A dielectric routing substrate 37 is over the array of biometric finger sensing pixels, the dummy pixel area 35, and the ground electrode 36. More particularly, the array of biometric finger sensing pixels, the dummy pixel area 35, and the ground electrode 36 are adjacent a bottom surface of the dielectric routing substrate 37.

The biometric finger sensor 30 includes an array shielding electrode 34 laterally outside the array of biometric finger sensing pixels 31 and is carried by an upper surface of the dielectric routing substrate 37. The array shielding electrode 34 is also illustratively in the shape of a square ring and may have a size ∈ of about 0.2 mm, for example (FIG. 5). Of course, in some embodiments, the array shielding electrode 34 may not be in the shape of a square ring and/or may have one or more discontinuities therein, and may have a different size.

The array shielding electrode 34 is coupled by a through-via 51 in the dielectric routing substrate 37. The array shielding electrode 34 is partially over the ground electrode 36.

The biometric finger sensor 30 illustratively includes a finger drive electrode 33 laterally outside the array shielding electrode 34. The finger drive electrode 33 is coupled by a conductive finger drive electrode pad 45 between the finger drive electrode 33 and the top surface of the dielectric routing substrate 37. In other words, the finger drive electrode 33 is carried by and coupled to the conductive finger drive electrode pad 45 which extends to the semiconductor substrate 32 by a through-via 52. A distance δ of about 0.1 mm may be between the finger drive electrode 33 and the array shielding electrode 34. An adhesive layer 41 may secure the finger drive electrode 33 to the dielectric routing substrate 37. In other words, the adhesive layer 41 is between the dielectric routing substrate 37 and the finger drive electrode 33.

The finger drive electrode 33 is also illustratively in the shape of a ring. Of course, in some embodiments, the finger drive electrode 33 may not be in the shape of a ring and/or may have one or discontinuities therein. A dielectric material 49 fills any open spaces between the components and connections (i.e. the array of finger sensing pixels 31, the dummy biometric finger sensing pixel area 35, the ground electrode 36, and the through-vias 51, 52).

A dielectric cap 38 is over the array of biometric finger sensing pixels 31, the dummy finger sensing pixel area 35, the ground electrode 36, the array shielding electrode 34, and the finger drive electrode 33. The dielectric cap 38 may be plastic, for example, and may be contoured for the user's finger. In other words, the dielectric cap 38 may have a curved upper surface 46 for receiving the user's finger 40 thereon during operation of the pushbutton switch 24. For example, the dielectric cap 38 may have a radius of curvature of 70 mm. In some embodiments, the finger drive electrode 33 may also have a curved upper surface, which may be particularly advantageous because the finger drive electrode is relatively close to the user's finger 40.

Of course, in some embodiments, the dielectric cap 38 may not have a curved upper surface or may have a relatively flat upper surface. Where, for example, the dielectric cap 38 has a flat upper surface, a dielectric material layer may be carried by the flat upper surface. The dielectric material may be z-axis anisotropic dielectric material, for example. Further details of a z-axis anisotropic dielectric material as it relates to a finger sensor are described in U.S. Pat. No. 6,088,471, which has a common inventor with and is assigned to the assignee of the present application, and the entire contents of which are herein incorporated by reference.

In some embodiments, the finger drive electrode 33 may be carried by or integrally formed with the dielectric cap 38. Thus, when the dielectric cap 38 is positioned over the array of biometric finger sensing pixels 31, the dummy finger sensing pixel area 35, the ground electrode 36, the array shielding electrode 34, and the conductive finger drive electrode pad 45, the finger drive electrode 33 contacts or couples to the conductive finger drive electrode pad.

The finger drive electrode 33 is configured to couple a finger drive signal through the user's finger 40 to the array of biometric finger sensing pixels 31. Of course, the finger drive electrode 33 may couple a finger drive signal through more than one user's finger, and more than one finger drive electrode may be used.

Finger drive circuitry 42 is coupled to finger drive electrode 33. The finger drive circuitry 42 may include a radio frequency drive signal generator, for example. The finger drive circuitry 42 generates the finger drive signal 47, which may be a 2 MHz finger drive signal. In some embodiments, the finger drive signal may be near 5 MHz, for example.

The finger drive circuitry 42 is also coupled to the array shielding electrode 34 and generates a compensating finger drive signal 48 for the array shielding electrode. The compensating finger drive signal 48 may have a different magnitude or offset with respect to the finger drive signal. In one particularly advantageous embodiment, the compensating finger drive signal 48 is in the form of an inverted finger drive signal for the array shielding electrode 34. In other words, the inverted finger drive signal is about 180-degrees out of phase with the finger drive signal for the finger drive electrode 33, as will be explained in further detail below.

As will be appreciated by those skilled in the art, the finger biometric sensing device 20 operates by injecting a small electrical signal, the finger drive signal 47, from the finger drive electrode 33 into the conductive layer of the skin of the user's finger 40. The shape of the electric field generated by that conductive layer of skin is then measured.

The finger drive electrode 33 is configured to inject the small electrical signal into the users' finger by operating as an insulated electrode finger drive, since the user's finger 40 does not come in direct contact with the finger drive electrode 33. In other words, the finger drive electrode 33 is separated from the surface of the user's finger 40 by a thickness of the dielectric cap 38. Electrical signals on an insulated finger drive electrode 33 couple capacitively to nearby skin surfaces. Signal attenuation due to coupling depends on the combination of several parameters including the area of the region of skin close to the electrode, the thickness of the dielectric cap 38 (i.e., the thickness of dielectric material between the finger drive electrode 33 and the user's finger 40), the electrical properties of the dielectric cap, and the electrical properties of the finger skin itself.

It may be important to note that the dielectric cap 38 being over the finger drive electrode 33, i.e., an insulated finger drive system, tends to reduce the variation in drive signal attenuation between the dry, thick skinned fingers and the moist, thin skinned fingers, for example, because of the increased distance between the user's finger 40 and the finger drive electrode. To address the difference in average attenuation, the voltage of the finger drive signal applied to the finger drive electrode 33 from the finger drive circuitry 42 may be increased. A typical voltage of the finger drive voltage may be upwards of 18 volts, for example. However, the biometric finger sensor 30 may demand significantly less dynamic range to be able to handle finger skin variation.

Moreover, because of the relatively small size of the biometric finger sensor 30, for example, so that it may be carried by the pushbutton switch 24 of the electronic device 20, voltage, for example, the finger drive signal, may leak from the finger drive electrode 33. This may cause distortion in the sensing field, and thus the biometric data sensed by the array of biometric finger sensing pixels 31. The finger drive circuitry 42 advantageously generates the inverted finger drive signal for the array shielding electrode 34 to reduce or cancel the leakage from the finger drive electrode 33. In other words, the array shielding electrode 34 reduces the field distortion or noise generated from the relatively close proximity of the finger drive electrode 33 to the array of biometric finger sensing pixels 31. Additionally, the ground electrode 36 reduces or blocks leakage from the array shielding electrode 34.

As will be appreciated by those skilled in the art, the above-described arrangement may be particularly advantageous for a relatively small-sized finger biometric sensor, for example, for use in a mobile electronic device. For example, an exemplary size α of the array of finger biometric sensing pixels 31 may be about 4.8 mm (FIG. 3). The length β of the biometric finger sensor 30 up to the finger drive electrode 33 may be 5.8 mm (FIG. 3). In other words, there may be a 1 mm between the array of finger biometric finger sensing pixels 31 and the finger drive electrode 33. The overall size or diameter γ of the biometric finger sensor 30 may be about 10.9 mm (FIG. 3). In other words the size of the finger drive electrode at its thickest part may be about 5.1 mm.

In some embodiments, the finger drive circuitry 42 may perform voltage balancing based upon a given one of the user's fingers. As will be appreciated by those skilled in the art, different fingers have different leakage profiles. The finger drive circuitry 42 may adjust the voltage of the finger drive signal and the inverted finger drive signal based upon the finger type. Of course, the finger drive circuitry 42 may perform other and/or additional balancing or compensation functions.

Figure 6:
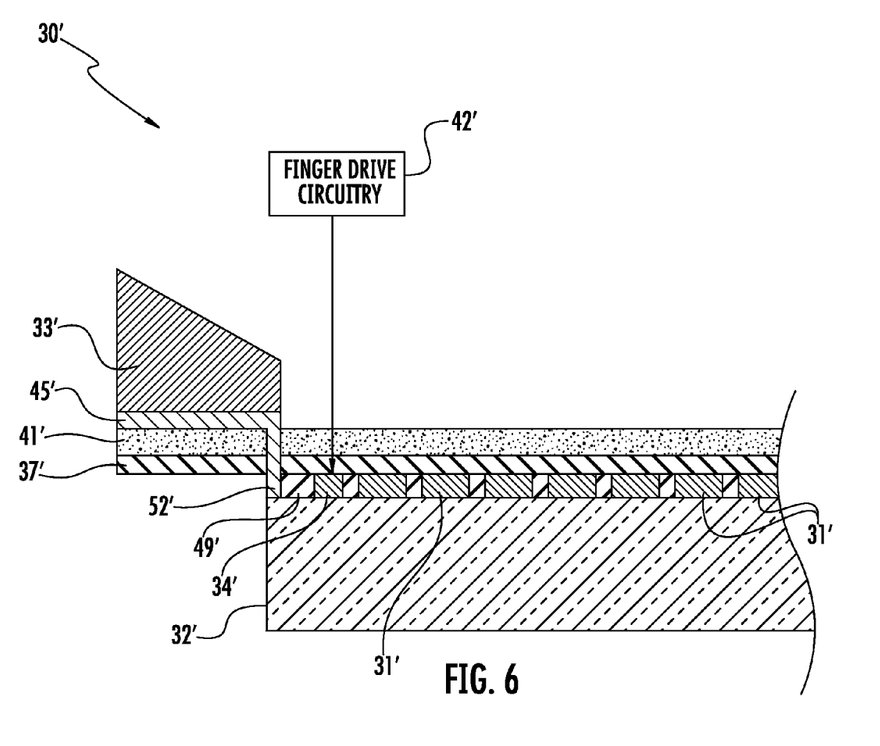
FIG. 6 is a cross-sectional view of a portion of a biometric finger sensor in accordance with another embodiment of the present invention.

Referring now to FIG. 6, in another embodiment, the array shielding electrode may be in the form of shielding pixels 34'. More particularly, the dummy biometric finger sensing pixel area and the ground electrode described above with respect to FIGS. 3-5, are replaced with shielding pixels 34' carried by the semiconductor substrate 32' and laterally outside the array of biometric finger sensing pixels 31'. The shielding pixels 34' are structurally similar to the biometric sensing pixels 31', but are configured so that they do no perform the function of sensing finger biometrics.

The finger drive circuitry 42', in addition to being coupled to the finger drive electrode 33', is coupled to the shielding pixels 34' and generates a compensating finger drive signal for the array shielding electrode. Similar to the embodiments described above, the compensating finger drive signal may have a different magnitude or offset with respect to the finger drive signal, and may be the form of an inverted finger drive signal for the shielding pixels 34'.

Figure 7:
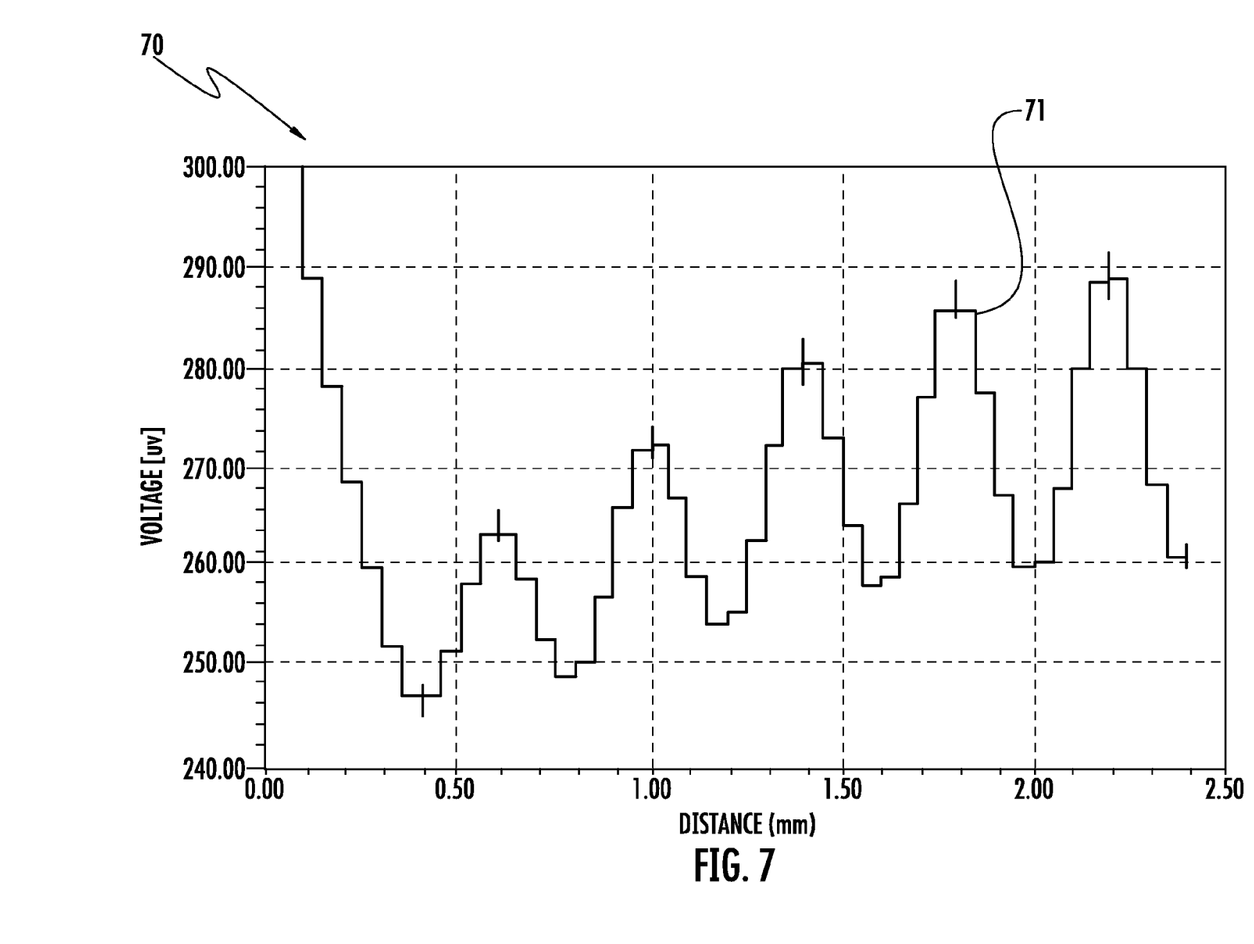
FIG. 7 is a graph of simulated voltage for a biometric finger sensor without an array shielding electrode.

Referring now to the graph 70 in FIG. 7, a pixel profile 71 is illustrated. Each horizontal flat spot in the profile is a pixel plate, as will be appreciated by those skilled in the art. The peaks correspond to ridges in the user's finger 40. The pixel profile illustrated is for a dry finger with no elevated field shaping electrode or array shielding electrode 34. It should be noted that the voltage corresponding to between 0 and about 0.4 mm is the effect of leakage from the drive signal. In other words, the voltage between 0 and 0.4 mm is undesirable. The remaining pixel profile in terms of voltage, from 0.4 mm to 2.5 mm rises because of the curvature of the substrate, as will be appreciated by those skilled in the art.

Figure 8:
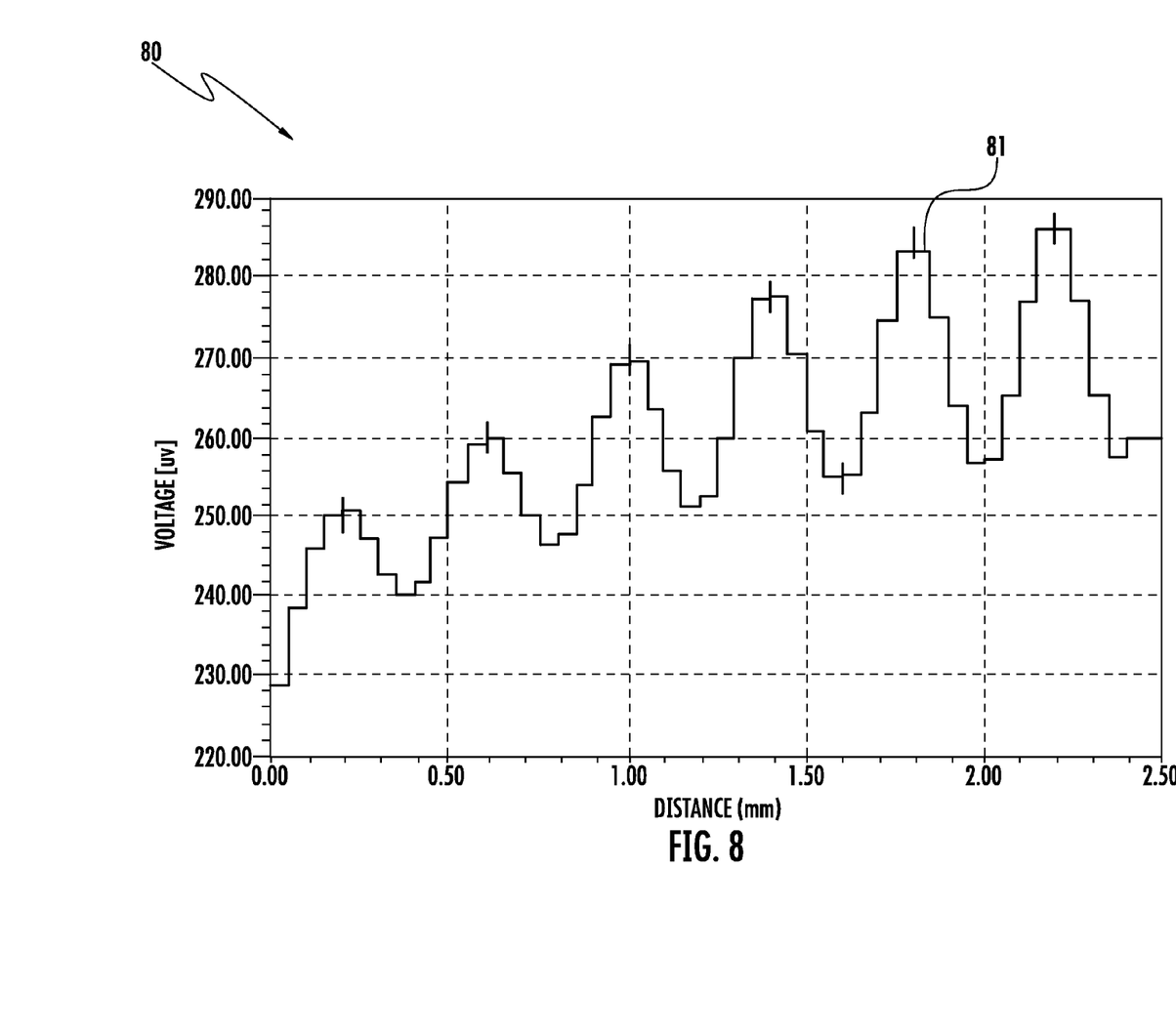
FIG. 8 is a graph of simulated voltage for a biometric finger sensor in accordance with the present invention.

Referring now to the graph 80 in FIG. 8, another pixel profile 81 is illustrated. The pixel profile is for a dry finger with an array shielding electrode 34 such that $V_{shield}=0.02*V_{drive}$. As will be appreciated by those skilled in the art, voltage leakage from the finger drive electrode is reduced.

A method aspect is directed to a method of making a biometric finger sensor 30. The method includes forming an array shielding electrode 34 outside an array of biometric finger sensing pixels 31 and forming a finger drive electrode 33 outside the array shielding electrode. The method further includes coupling finger drive circuitry 42 to generate a finger drive signal for the finger drive electrode 33 and generate an inverted finger drive signal for the array shielding electrode 34.

It should be noted that the biometric finger sensor described herein may be included within any electronic device, or may be used as a standalone biometric finger sensor to be coupled to or used in conjunction with other devices or circuitry. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A biometric finger sensor comprising:
an array of biometric finger sensing pixels capable of sensing biometric data;
an array shielding electrode outside and adjacent a periphery of said array of biometric finger sensing pixels;
a finger drive electrode outside said array shielding electrode; and
finger drive circuitry to generate a finger drive signal for said finger drive electrode and to invert the finger drive signal to generate an inverted finger drive signal for said array shielding electrode, the finger drive signal causing noise in the sensed biometric data based upon a proximity of the finger drive electrode to the array of biometric finger sensing pixels, and the inverted finger drive signal reducing the noise in the sensed biometric data.

2. The finger sensor of claim 1, wherein said array shielding electrode comprises a plurality of shielding pixels.

3. The finger sensor of claim 1, further comprising a ground electrode between said array shielding electrode and said array of biometric finger sensing pixels.

4. The finger sensor of claim 3, further comprising a dummy biometric finger sensing pixel area between said array of biometric finger sensing pixels and said ground electrode.

5. The finger sensor of claim 1, further comprising a dielectric routing substrate having a first surface adjacent said array of biometric finger sensing pixels, and a second surface adjacent said array shielding electrode and said finger drive electrode.

6. The finger sensor of claim 1, further comprising a dielectric cap over said array of biometric finger sensing pixels.

7. The finger sensor of claim 6, wherein said dielectric cap has a curved upper surface.

8. The finger sensor of claim 1, further comprising a semiconductor substrate carrying said array of biometric finger sensing pixels.

9. The finger sensor of claim 1, wherein said array of biometric finger sensing pixels comprises an array of electric field finger sensing pixels.

10. A mobile wireless communications device comprising:
a housing;
wireless communications circuitry carried by said housing;
an input device carried by housing;
a biometric finger sensor carried by said input device and comprising
an array of biometric finger sensing pixels capable of sensing biometric data,
an array shielding electrode outside and adjacent a periphery of said array of finger sensing pixels,
a finger drive electrode outside said array shielding electrode, and
finger drive circuitry to generate a finger drive signal for said finger drive electrode and to invert the finger drive signal to generate an inverted finger drive signal for said array shielding electrode, the finger drive signal causing noise in the sensed biometric data based upon a proximity of the finger drive electrode to the array of biometric finger sensing pixels, and the inverted finger drive signal reducing the noise in the sensed biometric data.

11. The electronic device of claim 10, wherein said array shielding electrode comprises a plurality of shielding pixels.

12. The electronic device of claim 10, wherein said biometric finger sensor further comprises a ground electrode between said array shielding electrode and said array of biometric finger sensing pixels.

13. The electronic device of claim 12, wherein said biometric finger sensor further comprises a dummy biometric finger sensing pixel area between said array of biometric finger sensing pixels and said ground electrode.

14. The electronic device of claim 10, wherein said biometric finger sensor further comprises a dielectric routing substrate having a first surface adjacent said array of biometric finger sensing pixels, and a second surface adjacent said array shielding electrode and said finger drive electrode.

15. The electronic device of claim 10, wherein said input device comprises a pushbutton switch.

16. The electronic device of claim 10, wherein said biometric finger sensor further comprises a dielectric cap over said array of biometric finger sensing pixels, said finger drive electrode, and said finger drive circuitry.

17. The electronic device of claim 16, wherein said dielectric cap has a curved upper surface.

18. The electronic device of claim 10, wherein said biometric finger sensor further comprises a semiconductor substrate carrying said array of biometric finger sensing pixels.

19. The electronic device of claim 10, further comprising a processor coupled to said biometric finger sensor for performing at least one authentication function.

20. The electronic device of claim 19, wherein said processor is to perform the at least one authentication function based upon operation of said at least one input device.

21. A method of making a biometric finger sensor comprising:
forming an array shielding electrode outside and adjacent a periphery of an array of biometric finger sensing pixels;
forming a finger drive electrode outside the array shielding electrode; and
coupling finger drive circuitry to generate a finger drive signal for the finger drive electrode and to invert the finger drive signal to generate an inverted finger drive signal for the array shielding electrode, the finger drive signal causing noise in sensed biometric data based upon a proximity of the finger drive electrode to the array of biometric finger sensing pixels, and the inverted finger drive signal reducing the noise in the sensed biometric data.

22. The method of claim 21, wherein forming the array shielding electrode comprises forming a plurality of shielding pixels.

23. The method of claim 21, further comprising forming a ground electrode between the array shielding electrode and the array of biometric finger sensing pixels.

24. The method of claim 23, further comprising forming a dummy biometric finger sensing pixel area between the array of biometric finger sensing pixels and the ground electrode.

25. The method of claim 21, further comprising positioning a dielectric routing substrate having a first surface adjacent the array of biometric finger sensing pixels, and a second surface adjacent the array shielding electrode and the finger drive electrode.

26. The method of claim 21, further comprising positioning a dielectric cap over the array of biometric finger sensing pixels, the finger drive electrode, and the finger drive circuitry.

27. The method of claim 26, wherein the dielectric cap has a curved upper surface.

* * * * *

UNITED STATES PATENT AND TRADEMARK OFFICE
CERTIFICATE OF CORRECTION

PATENT NO.        : 9,322,794 B2
APPLICATION NO.   : 13/718307
DATED             : April 26, 2016
INVENTOR(S)       : Setlak et al.

Page 1 of 1

It is certified that error appears in the above-identified patent and that said Letters Patent is hereby corrected as shown below:

In the Claims

| | |
|---|---|
| Claim 10, Column 9, Line 53 | Delete: "an input device carried by housing" Insert: -- an input device carried by said housing -- |
| Claim 25, Column 10, Line 63-64 | Delete: "comprising a positioning" Insert: -- comprising positioning -- |

Signed and Sealed this
Twenty-eighth Day of June, 2016

Michelle K. Lee
*Director of the United States Patent and Trademark Office*